(12) United States Patent
Labadie et al.

(10) Patent No.: US 7,135,470 B2
(45) Date of Patent: Nov. 14, 2006

(54) THIENOPYRIDAZINES AS IKK INHIBITORS

(75) Inventors: Sharada Shenvi Labadie, Sunnyvale, CA (US); Eric Brian Sjogren, Mountain View, CA (US); Francisco Xavier Talamas, Mountain View, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/121,807

(22) Filed: May 4, 2005

(65) Prior Publication Data

US 2005/0272730 A1 Dec. 8, 2005

Related U.S. Application Data

(60) Provisional application No. 60/568,372, filed on May 4, 2004.

(51) Int. Cl.
*C07D 491/048* (2006.01)
*C07D 495/04* (2006.01)
*A61K 31/5025* (2006.01)

(52) U.S. Cl. .................. 514/234.2; 544/177; 544/235; 514/248

(58) Field of Classification Search ............. 544/235, 544/117; 514/248, 234.2
See application file for complete search history.

(56) References Cited

U.S. PATENT DOCUMENTS 6,232,320 B1  5/2001  Stewart et al.
6,579,882 B1  6/2003  Stewart et al.
2001/0020030 A1  9/2001  Stewart et al.
2004/0097485 A1  5/2004  Burkitt et al.

FOREIGN PATENT DOCUMENTS

WO   WO 00/75145 A1   12/2000
WO   WO 02/072549 A1   9/2002

OTHER PUBLICATIONS

Robert Smith, Drug Discovery Today (DDT), vol. 10, No. 23/24, Dec. 2005, pp. 1598-1604.*

* cited by examiner

*Primary Examiner*—Kahsay Habte
(74) *Attorney, Agent, or Firm*—Grant D. Green

(57) ABSTRACT

The invention provides compounds of the formula I:

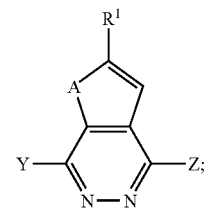

or pharmaceutically acceptable salts, solvates or prodrugs thereof, wherein: A, Y, Z and $R^1$ are as defined herein. Also provided are compositions comprising, methods of preparing, and methods for using the subject compounds.

16 Claims, No Drawings

THIENOPYRIDAZINES AS IKK INHIBITORS

CROSS REFERENCE TO RELATED APPLICATIONS

This application claims benefit under 35 U.S.C. 119(e) of U.S. Provisional Application No. 60/568,372 filed May 4, 2004, which is hereby incorporated by reference in its entirety.

BACKGROUND OF THE INVENTION

Tumor Necrosis Factor (TNF) and interleukin-1 (IL-1) have been associated with a wide range of biological processes, including inflammation. Recruitment of immune cells to sites of injury involves the concerted interactions of a large number of soluble mediators, and several cytokines appear to play key roles in these processes, particularly IL-1 and TNF. Both of these cytokines are derived from mononuclear cells and macrophages, along with other cell types. IL-1 and TNF produce many of the same proinflammatory responses, including fever, sleep and anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. IL-1 and TNF also contribute to the tissue degeneration arising from chronic inflammatory conditions, such as stimulation of fibroblast proliferation and induction of collagenase. These cytokines have also been implicated in the process of bone resorption and adipose tissue regulation. Thus, IL-1 and TNF play key roles in a large number of pathological conditions, including rheumatoid arthritis, inflammatory bowel disease, diabetes, obesity, bone mass loss, cancer, neurological conditions such as ischemic stroke or closed head injuries NF-κB is a heterodimeric transcription transcription factor regulating the expression of multiple inflammatory genes. The expression of more than 70 known proteins is transcriptionally regulated by the binding of NF-κB to specific sequence elements in the promoter region of these genes (Baeuerle and Baichwal, Advances in Immunology 65:111–137, 1997) NF-κB has been implicated in many pathophysiologic processes including angiogenesis (Koch et al., Nature 376:517–519, 1995), atherosclerosis (Brand et al., J Clin Inv. 97:1715–1722, 1996), endotoxic shock and sepsis (Bohrer et al., J. Clin. Inv. 100: 972–985, 1997), inflammatory bowel disease (Panes et al., Am J. Physiol. 269:H1955–H1964, 1995), ischemia/reperfusion injury (Zwacka et al., Nature Medicine 4: 698–704, 1998), and allergic lung inflammation (Gosset et al., Int Arch Allergy Immunol. 106: 69–77, 1995). Many immune and inflammatory mediators including TNF.alpha., lipopolysaccharide (LPS), IL-1, anti-CD28, CD40L, FasL, viral infection, and oxidative stress have been shown to lead to NF-κB activation. Because of the central role of NF-κB in inflammatory disease, inhibition of NF-κB by targeting regulatory proteins in the NF-κB activation pathway represents an attractive strategy for generating anti-inflammatory therapeutics.

The IκB kinases (IKKs) are key regulatory signaling molecules coordinating the activation of NF-κB. The NFκB heterodimer in its active state is held in the cytoplasm by association with inhibitory IκB proteins (Huxford et al. *Cell*, 95, 759 (1998); Jacobs et al. *Cell*, 95, 749 (1998)). Treatment of cells with IL-1 or TNF leads to activation of intracellular signal transduction pathways that in turn lead to phosphorylation of IκB proteins on specific amino acid residues (serines 32 and 36 in IκBα, serines 19 and 23 in IκB β). Mutation of one or both serine residues renders IκB resistant to cytokine-induced phosphorylation. This signal-induced phosphorylation targets IκB for proteosome-mediated degradation, allowing nuclear translocation of NF-κB (Thanos and Maniatis, *Cell*, 80, 529 (1995)). The only regulated step in the IκB degradation pathway is the phosphorylation of IκB by IκB (IKK) kinases (Yaron et al. *EMBO J.* 16, 6486 (1997)).

The kinases IKKα and IKKβ have been identified as the most likely mediators of TNF- and IL-1-induced IκB phosphorylation and degradation, which results in NF-κB activation and upregulation of families of genes involved in inflammatory processes (Woronicz et al. *Science* (1997); Karin, *Oncogene* 18, 6867 (1999); Karin, *J. Biol. Chem.* 274, 27339 (1999)). IKKα and IKKβ have very similar primary structures, displaying more than 50% overall sequence identity. In the kinase domain, their sequences are 65% identical.

Because of the important role played by TNF and IL-1 in many pathological conditions, and the involvement of IKKα and IKKβ in the signal transduction of both TNF and IL-1, there is a need for compounds that potently and selectively inhibit either of these IKK kinases, as well as treatments or therapies using such compounds. The present invention satisfies these needs.

SUMMARY

The invention provides compounds of the formula I:

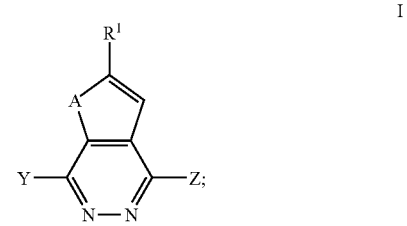

or a pharmaceutically acceptable salt, solvate or prodrug thereof, wherein:
  $R^1$ is aryl or heteroaryl;
  A is S or O;
  one of Y and Z is —$NR^2R^3$, and the other is —C(O)$NR^4R^5$; and
  $R^2$, $R^3$, $R^4$, and $R^5$ each independently is hydrogen or alkyl.

The invention further provides compositions comprising, methods of preparing, and methods for using the aforementioned compounds.

DETAILED DESCRIPTION OF THE INVENTION

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms (i.e., "$C_1$–$C_6$alkyl"). Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH=CH—), 2,2-dimethylethenylene, propenylene, 2-methylpropenylene, butenylene, pentenylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylene" means a divalent aryl radical wherein aryl is as defined herein. "Arylene" includes, for example, ortho-, meta- and para-phenylene (1,2-phenylene, 1,3-phenylene and 1,4-phenylene respectively), which may be optionally substituted as defined herein.

"Arylalkyl" and "Aralkyl", which may be used interchangeably, mean a radical —$R^a R^b$ where $R^a$ is an alkylene group and $R^b$ is an aryl group as defined herein; e.g., benzyl, phenylethyl, 3-(3-chlorophenyl)-2-methylpentyl, and the like are examples of arylalkyl.

"Cycloalkyl" means a saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^b R^c$, and —$S(O)_n R^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic monovalent radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyridinyl, pyridazyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylene" means a divalent heteroaryl radical wherein heteroaryl is as defined herein. "Heteroarylene" may be optionally substituted as defined herein. "Heteroarylene" includes, for example, indolylene, pyrimidinylene, and the like.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Optionally substituted", when used in association with "aryl", "arylene", phenyl", "phenylene", "heteroaryl", heteroarylene or "heterocyclyl", means an aryl, arylene, phenyl, phenylene, heteroaryl, heteroarylene, or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$^n$— CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl.

The terms "modulate", "modulation" and the like refer to the ability of a compound to increase or decrease the function and/or expression of IKK, where IKK function may include kinase activity and/or protein-binding. Modulation may occur in vitro or in vivo. Modulation, as described herein, includes the inhibition or activation of IKK function and/or the downregulation or upregulation of IKK expression, either directly or indirectly. A modulator preferably activates IKK function and/or upregulates IKK expression. More preferably, a modulator activates or inhibits IKK function and/or upregulates or downregulates IKK expression. Most preferably, a modulator inhibits IKK function and/or downregulates IKK expression. The ability of a compound to inhibit IKK function can be demonstrated in an enzymatic assay or a cell-based assay (e.g., inhibition of IL-1-stimulated NF-κB activation).

As used herein, the term "IKK-mediated condition or disease" and related terms and phrases refer to a condition or disorder characterized by inappropriate, e.g., less than or greater than normal, IKK activity. Inappropriate IKK functional activity might arise as the result of IKK expression in cells which normally do not express IKK, increased IKK expression (leading to, e.g., inflammatory and immunoregulatory disorders and diseases) or decreased IKK expression. An IKK-mediated condition or disease may be completely or partially mediated by inappropriate IKK functional activity. However, an IKK-mediated condition or disease is one in which modulation of IKK results in some effect on the underlying condition or disorder (e.g., an IKK inhibitor results in some improvement in patient well-being in at least some patients).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:
  acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or
  salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p 1–92, Elesevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to cho0se a group for the ease of removal and for the ability to withstand the following reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity of the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature.

Chemical structures shown herein were prepared using ISIS® version 2.2. Any open valency appearing on a carbon, oxygen or nitrogen atom in the structures herein indicates the presence of a hydrogen.

Compounds of the Invention

The invention provides compounds of the formula I:

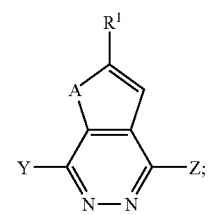

or a pharmaceutically acceptable salt, solvate or prodrug thereof, wherein:
$R^1$ is aryl or heteroaryl;
A is S or O;
one of Y and Z is —$NR^2R^3$, and the other is —C(O) $NR^4R^5$; and
$R^2$, $R^3$, $R^4$, and $R^5$ each independently is hydrogen or alkyl.

In embodiments of the invention where any of $R^1$, $R^2$, $R^3$, $R^4$ and $R^5$ are alkyl or contain an alkyl moiety, such alkyl is preferably lower alkyl, i.e. $C_1$–$C_6$alkyl, and more preferably $C_1$–$C_4$alkyl.

It should be understood that the scope of this invention encompasses not only the various isomers which may exist but also the various mixture of isomers which may be formed. Furthermore, the scope of the present invention also encompasses solvates and salts of compounds of formula I.

In many embodiments of the invention, A is S or O, and in certain embodiments A is S.

In many embodiments of the invention, $R^1$ is phenyl, naphthyl, thienyl or pyridyl, each optionally substituted, and in certain embodiments $R^1$ is optionally substituted phenyl or optionally substituted naphthyl.

In many embodiments $R^2$, $R^3$, $R^4$ and $R^5$ are hydrogen.

In certain embodiments Y is —C(O)NH$_2$ or —CN, and Z is —NH$_2$.

In some specific embodiments $R^1$ is phenyl, naphthyl, 4-fluorophenyl, 4-methoxyphenyl, 4-hydroxyphenyl, 4-(2-cyanoethyl)-phenyl, 3-nitrophenyl, 5-cyano-2-fluorophenyl, 5-cyano-3-fluorophenyl, 3-cyano-4-(morpholin-4-ylmethyl)-phenyl, or 4-(morpholin-4-ylmethyl)-phenyl.

In certain embodiments the compounds of the invention may be of the formula II:

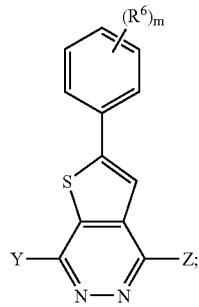

wherein:
m is from 0 to 4;
each $R^6$ independently is halo, alkyl, alkoxy, haloalkyl, nitro, cyano, 2-cyanoethyl, or morpholinomethyl; and
Y and Z are as recited in claim 1.

In certain embodiments of formula II, $R^3$, $R^4$, $R^5$ and $R^6$ are hydrogen. In some embodiments Y is —C(O)NH$_2$ or —CN, and Z is —NH$_2$. In certain embodiments m is 0, while in other embodiments m is 1 and $R^6$ is halo, alkyl, alkoxy, haloalkyl, nitro, cyano, 2-cyanoethyl, or morpholinomethyl.

In certain embodiments the subject compounds are of the formula III:

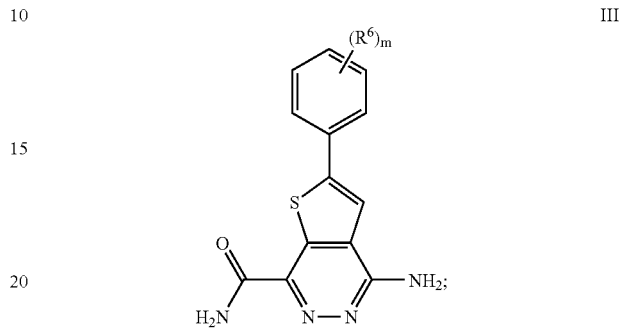

wherein m and $R^6$ are as defined herein.

In certain embodiments of formula III m is 0, while in other embodiments m is 1 and $R^6$ is halo, alkyl, alkoxy, haloalkyl, nitro, cyano, 2-cyanoethyl, or morpholinomethyl.

Representative compounds in accordance with the invention are shown in Table 1 together with melting point or mass spectrum M+H.

TABLE 1

| # | Structure | Name | MP° C./ M + H |
|---|-----------|------|---------------|
| 1 | 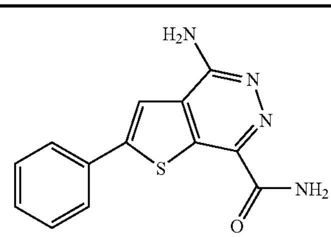 | 4-Amino-2-phenyl-thieno[2,3-d]pyridazine-7-carboxylic acid amide | 271 |
| 2 | 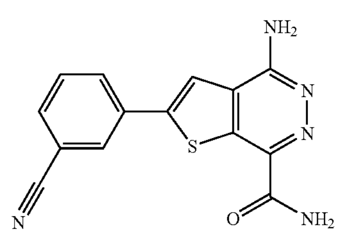 | 4-Amino-2-(3-cyano-phenyl)-thieno[2,3-d]pyridazine-7-carboxylic acid amide | >300° C. |
| 3 | 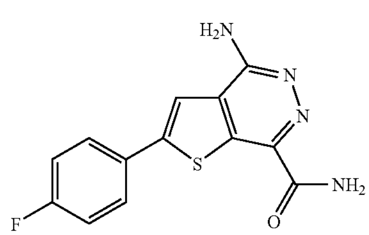 | 4-Amino-2-(4-fluoro-phenyl)-thieno[2,3-d]pyridazine-7-carboxylic acid amide | 289 |

TABLE 1-continued

| # | Structure | Name | MP° C./ M + H |
|---|---|---|---|
| 4 | 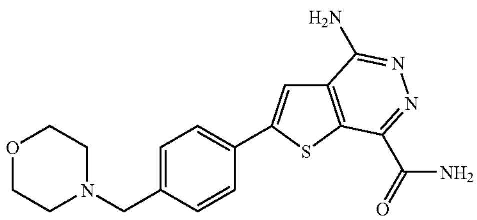 | 4-Amino-2-(4-morpholin-4-ylmethyl-phenyl)-thieno[2,3-d]pyridazine-7-carboxylic acid amide | 370 |

Another aspect of the invention provides a composition comprising a therapeutically effective amount of at least one compound of formula (I) and a pharmaceutically acceptable carrier.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Referring now to Scheme A below, there is shown a synthetic procedure for making compounds of the invention, wherein m, $R^2$, $R^3$, $R^4$, $R^5$ and $R^6$ are as described above.

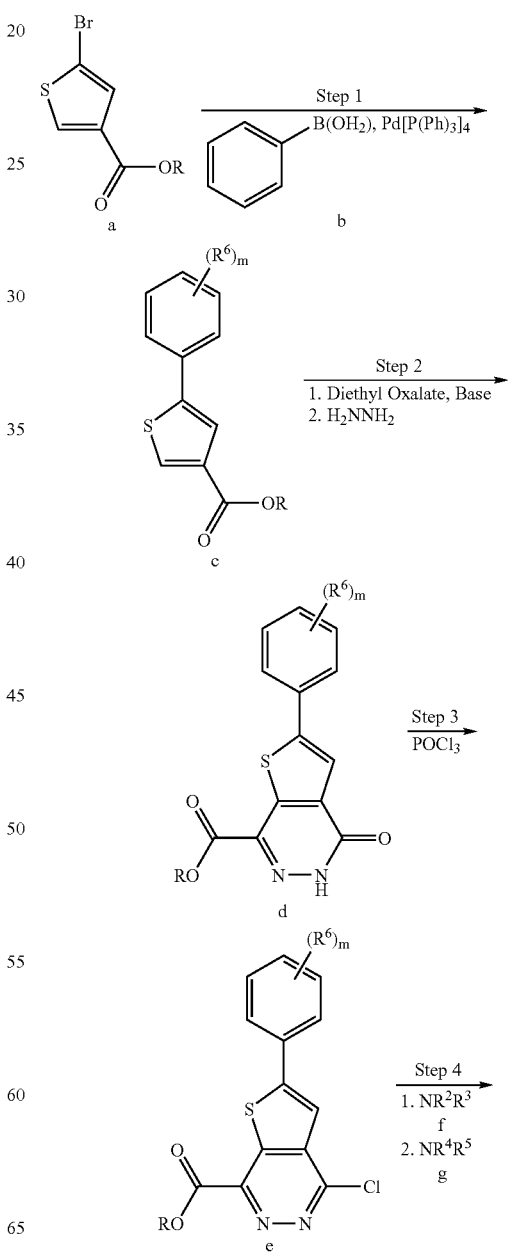

SCHEME A

-continued

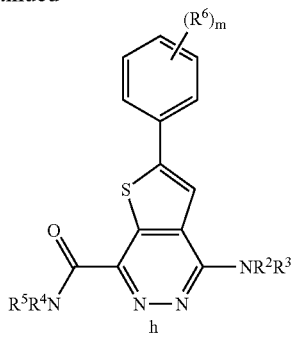

In step 1 of Scheme A, 5-bromothiophene-3-carboxylic acid ester a, where R is methyl ethyl or other alkyl, is alkylated with a phenyl boronic acid compound b in the presence of a palladium catalyst in the manner described above for Scheme A, to provide phenyl thiophene carboxylic acid ester c. In step 2, compound c is treated with diethyl oxalate in the presence of strong base such as lithium diisopropylamide under dry, polar aprotic conditions, followed by treatment with hydrazine under aqueous conditions, to afford a tetrahydrothienopyridazinone compound d. Tetrahydrothienopyridazinone d is then reacted in step 3 with phosporous oxychloride to form phenyl thienopyridazine compound e. In step 4, the compound e is first reacted with amine f under dry, polar aprotic conditions, and then with amine g under aqueous conditions to provide thienopyridazine compound h, which is a compound of formula I in accordance with the invention.

Many variations on the procedure of Scheme A are possible and will suggest themselves to those skilled in the art. For example, 5-bromothiophene-3-carboxylic acid ester a in step 1 may be replaced with 5-bromofuran-carboxylic acid ester, to afford compounds of formula I wherein A is O rather than S. Similarly, 5-bromothiophene-3-carboxylic acid ester a may be replaced with 5-bromothiophene-2-carboxylic acid ester or 5-bromofuran-2-carboxylic acid ester, to effectively change the locate of the S or O heteroatom within the final product h.

More specific details for producing compounds of formula I are described in the Examples section below.

Utility

The compounds of the invention are useful of treating IKK-mediated conditions or diseases by administering to a subject having such a disease or condition, a therapeutically effective amount of a compound or composition of the invention.

Diseases and conditions associated with inflammation, infection and cancer can be treated with the present compounds and compositions. In one group of embodiments, diseases or conditions, including chronic diseases, of humans or other species can be treated with inhibitors of IKK function. These diseases or conditions include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome); (5) in another group of embodiments, diseases or conditions are treated with inhibitors of IKK function that will promote cell death; examples of these diseases include, but are not limited to, neoplastic diseases such as solid tumors, skin cancer, melanoma, lymphoma, and diseases in which angiogenesis and neovascularization play a role; (6) other metabolic disorders that are sensitive to inhibition of TNF or IL-1 signaling, such as obesity for example.

Testing

The pharmacology of the compounds of this invention was determined by art recognized procedures. The in vitro techniques for determining the affinities of test compounds are described in the Examples below.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a presurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

EXAMPLES

The following preparations and examples are given to enable those skilled in the art to more clearly understand and to practice the present invention. They should not be considered as limiting the scope of the invention, but merely as being illustrative and representative thereof.

Example 1

4-Amino-2-(4-fluorophenyl)-thieno[2,3-d]pyridazine-7-carboxylic acid amide

The synthetic procedures described in this Example were carried out according to the process shown in Scheme B.

SCHEME B

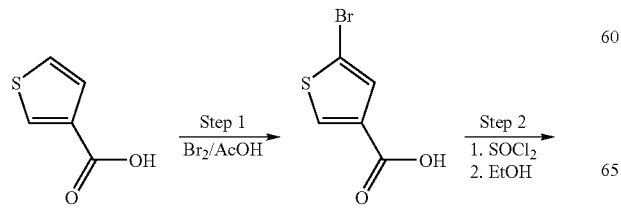

-continued

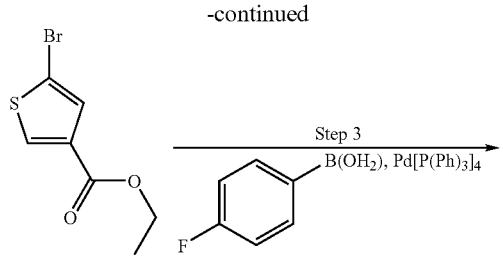

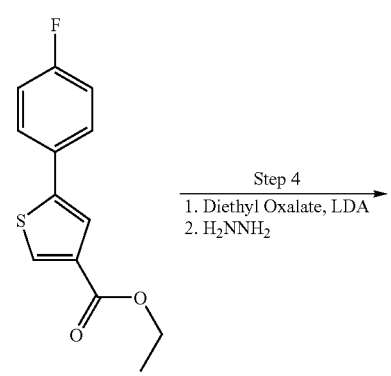

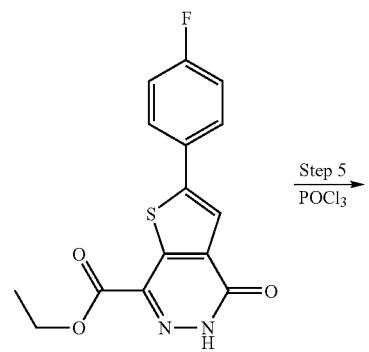

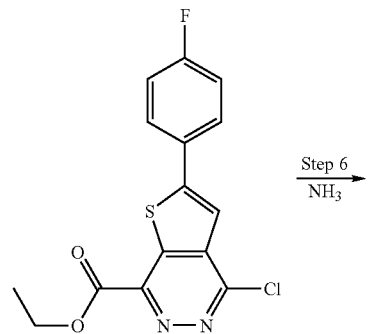

-continued

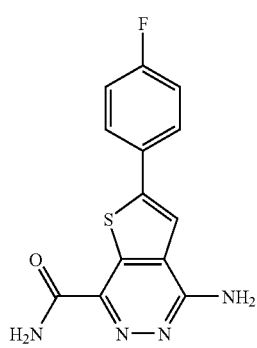

Step 1

5-Bromo-thiophene-3-carboxylic acid

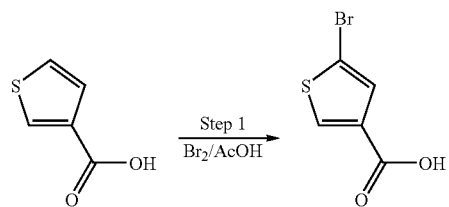

To a solution of thiophene-3-carboxylic acid (25 g, 195 mmol) in AcOH (700 ml) was added bromine (10.6 ml) in AcOH (200 ml) dropwise. After the addition, the reaction was stirred for 30 minutes at room temperature and poured onto water. A white precipitate was formed, which was filtered and dried to obtain 5-bromo-thiophene-3-carboxylic acid (14.5 g) as a white solid after crystallization (water).

Step 2

5-Bromo-thiophene-3-carboxylic acid ethyl ester

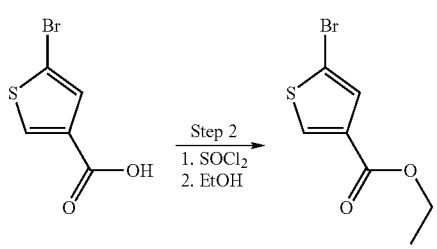

A solution of 5-bromo-thiophene-3-carboxylic acid (14.5 g, 70 mmol) was dissolved in SOCl$_2$ and the mixture was refluxed for 2 hours. The mixture was concentrated under reduced pressure to give a yellow oil. The oil was was dissolved in EtOH and the mixture was refluxed for 1 hour, then concentrated under reduced pressure to give 5-bromo-thiophene-3-carboxylic acid ethyl ester as an oil (16.46 g, quantitative).

Step 3

5-(4-Fluorophenyl)-3-thiophenecarboxylic acid ethyl ester

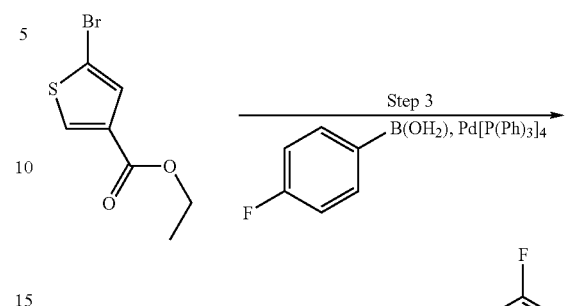

A mixture of 5-bromo-thiophene-3-carboxylic acid ethyl ester (1.0 g, 4.5 mmol), 4-fluorophenylboronic acid (0.88 g, 6.4 mmol), potassium carbonate (1.75 g, 12 mmol) and tetrakistriphenylphosphinepalladium(0) (0.2 g, 4 mole %) in a 50:50 mixture of DME/H$_2$O (10 mL) was heated at reflux temperature overnight under a nitrogen atmosphere. The resulting reaction mixture was cooled, diluted with ethyl acetate and washed with water. The organic layer was washed with brine, dried over sodium sulfate and rotary evaporated. The residue was purified by flash chromatography (silica gel; 2% acetone/hexane) to obtain 5-(4-fluorophenyl)-3-thiophenecarboxylic acid ethyl ester as an oil (1.0 g, 88%). MS: m/z=251 (M+1).

Step 4

2-(4-Fluoro-phenyl)-4-oxo-4,5-dihydro-thieno[2,3-d]pyridazine-7-carboxylic acid ethyl ester

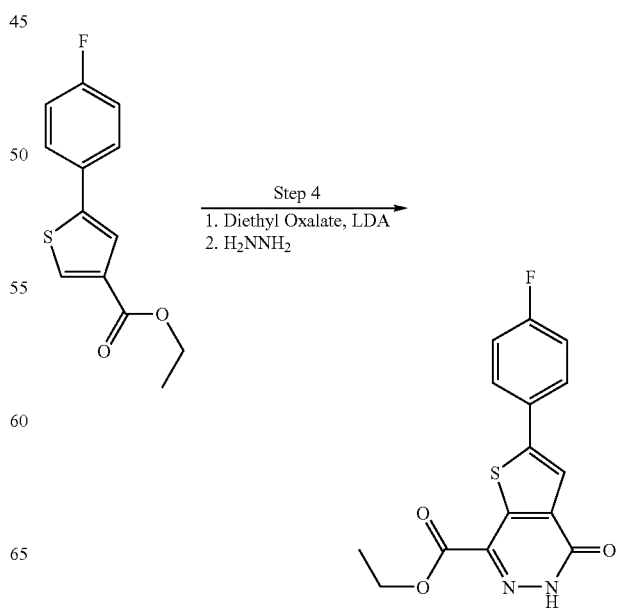

A mixture of 5-(4-fluorophenyl)-3-thiophenecarboxylic acid ethyl ester (1.0 g, 4.0 mmol) and diethyl oxalate (1.16 g, 8.0 mmol) in dry THF (40 mL) was cooled in dry-ice acetone bath and a solution of LDA in THF (2.0 mL, 4 mmol) was added dropwise. The reaction mixture was stirred for 10 minutes at ice bath temperature and then quenched with dilute HCl and warmed to room temperature. The reaction mixture was diluted with water, washed with water, brine and dried over sodium sulfate. The residue obtained after evaporation was purified by flash chromatography (silica gel; 2% acetone/hexane) to obtain an oil (0.8 g). This oil was dissolved in ethanol (10 mL) and hydrazine hydrate (200 uL) was added. The mixture was heated at 60° C. for 10 minutes and cooled to room temperature and allowed to react for 30 minutes. The solid was collected by filtration and washed with dichloromethane/hexane mixture. The solid was then stirred over 5% methanol/dichloromethane and filtered. The filtrate was concentrated to obtain 2-(4-fluoro-phenyl)-4-oxo-4,5-dihydro-thieno[2,3-d]pyridazine-7-carboxylic acid ethyl ester ester as a solid (0.2 g). MS: m/z=321 (M+1).

Step 5

4-Chloro-2-(4-fluorophenyl)-thieno[2,3-d]pyridazine-7-carboxylic acid ethyl ester

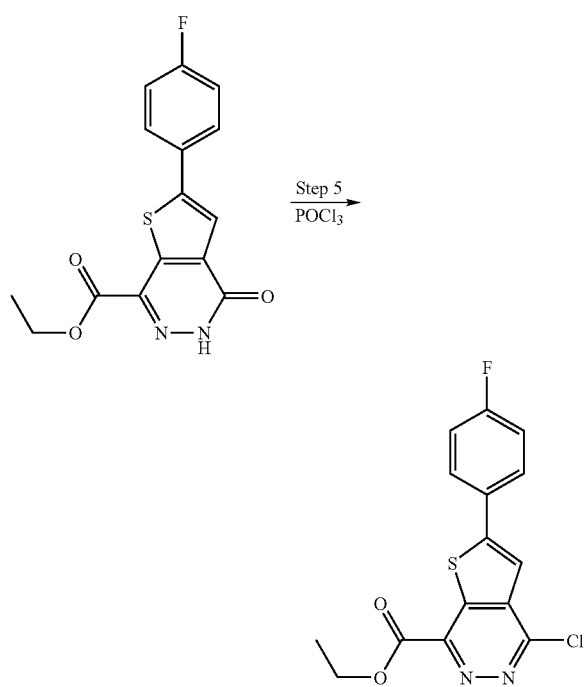

A mixture of 2-(4-fluoro-phenyl)-4-oxo-4,5-dihydro-thieno[2,3-d]pyridazine-7-carboxylic acid ethyl ester (0.2 g, mmol) in phosphorous oxychloride (3 mL) was heated at 90° C. for 3 hours, cooled and evaporated to dryness. To the residue was added ice and ethyl acetate and then basified over potassium carbonate solid. The organic layer was separeted, washed with water, brine and dried over sodium sulfate. The organic layer was evaporated to dryness and the residue was purified by flash chromatography (silica gel, 5% acetone/hexane) to obtain 4-chloro-2-(4-fluorophenyl)-thieno[2,3-d]pyridazine-7-carboxylic acid ethyl ester as a solid (0.12 g). MS: m/z=338 (M+1).

Step 6

4-Amino-2-(4-fluorophenyl)-thieno[2,3-d]pyridazine-7-carboxylic acid amide

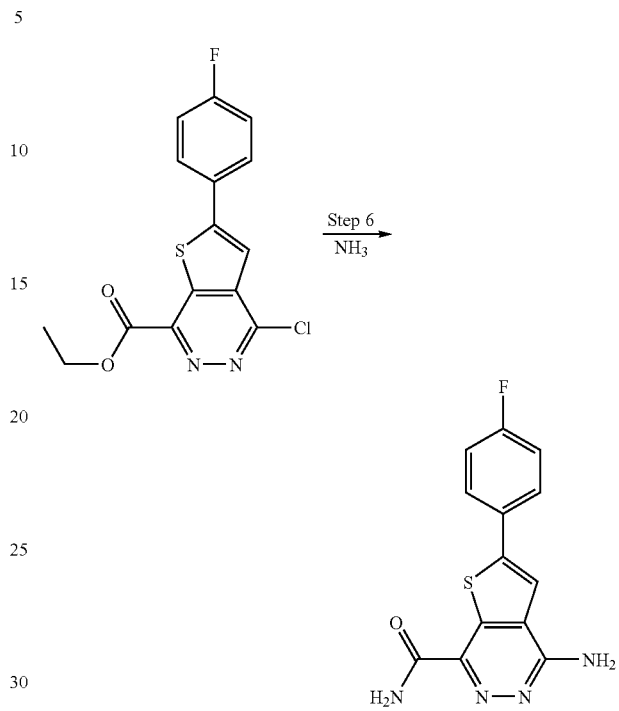

4-Chloro-2-(4-fluorophenyl)-thieno[2,3-d]pyridazine-7-carboxylic acid ethyl ester was dissolved in ammoniacal dioxane (5 mL) which was prepared by bubbling ammonia into dioxane while cooling in dry-ice/acetone. The resulting mixture was heated at 80° C. for 20 hours. The mixture was cooled and solvent was removed under vacuum. The residue was purified by flash chromatography (silica gel, 2% MeOH/dichloromethane) to yield a white solid. This solid was then suspended in aqueous ammonium hydroxide and heated overnight. The reaction mixture was cooled, stripped and purified (silica gel, 2% MeOH/dichloromethane) to obtain 4-Amino-2-(4-fluorophenyl)-thieno[2,3-d]pyridazine-7-carboxylic acid amide (0.01 g). MS: m/z=289 (M+1).

Additional compounds prepared by the procedure of Example 1 are shown in Table 1.

Example 2

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
|---|---|
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 3

This example describes an assay that is useful in evaluating and selecting a compound that modulates IKK. The assay measures the incorporation of radiolabeled $^{33}$P gATP into the Biotin-peptide kinase substrate, derived from the IkB-alpha sequence.

In a 40 ul volume, 26 ul of ADB diluted, purified recombinant human IKKb [25 nM] was mixed with 4 ul 10× concentration of test compounds, [usually 100 uM–0.003 uM], [10%] DMSO and incubated for 10 minutes at room temperature. The kinase reaction was initiated by the addition of 10 ul 4× substrate cocktail containing the peptide substrate [0 or 30 μM] ATP [10 μM], and $^{33}$PgATP [2uCi/rxn]. After 30 minutes of incubation at 30° C., the reaction was terminated by the transfer of 25 ul reaction sample to a phosphocellulose membrane/plate containing 150 ul 0.75% phosphoric acid.

On the following day, the free radionucleotides in the phosphocellulose membrane were washed under vacuum with 3×200 ul of 0.75% phosphoric acid. After the last wash membrane/plates were transferred to an adoptor plate and 70 ul of scintillation cocktail was added to each well. After four hours, the amount of radioactivity for each well was counted in a top counter.

The compounds of the invention were active using the above assay. Many compounds displayed $IC_{50}$ values of less than or equal to about 10 μM in the above assay. The compound 4-Amino-2-(4-fluoro-phenyl)-thieno[2,3-d]pyridazine-7-carboxylic acid amide, exhibited $IC_{50}$ values of less than 1 μM.

While the present invention has been described with reference to the specific embodiments thereof, it should be

What is claimed is:

1. A compound of formula I:

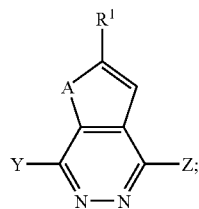

or a pharmaceutically acceptable salt, solvate or prodrug thereof,
wherein:
$R^1$ is aryl or heteroaryl;
A is S or O;
one of Y and Z is —$NR^2R^3$, and the other is —$C(O)NR^4R^5$; and
$R^2$, $R^3$, $R^4$, and $R^5$ each independently is hydrogen or alkyl.

2. The compound or claim 1, wherein A is S.

3. The compound of claim 2, wherein $R^1$ is phenyl, naphthyl, thienyl or pyridyl, each optionally substituted.

4. The compound of claim 2, wherein $R^1$ is optionally substituted phenyl.

5. The compound of claim 4, wherein $R^2$, $R^3$, $R^4$ and $R^5$ are hydrogen.

6. The compound of claim 4, wherein Y is —$C(O)NH_2$ and Z is —$NH_2$.

7. The compound of claim 6, wherein $R^1$ is phenyl, naphthyl, 4-fluorophenyl, 4-methoxyphenyl, 4-hydroxyphenyl, 4-(2-cyanoethyl)-phenyl, 3-nitrophenyl, 5-cyano-2-fluorophenyl, 5-cyano-3-fluorophenyl, 3-cyano-4-(morpholin-4-ylmethyl)-phenyl, or 4-(morpholin-4-ylmethyl)-phenyl.

8. The compound of claim 1, wherein said compound is of the formula II:

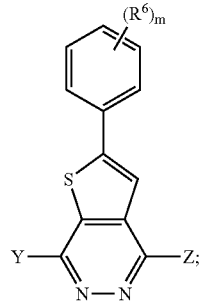

wherein:
m is from 0 to 4;
each $R^6$ independently is halo, alkyl, alkoxy, haloalkyl, nitro, cyano 2-cyanoethyl, or morpholinomethyl; and
Y and Z are as recited in claim 1.

9. The compound of claim 8, wherein $R^2$, $R^3$, $R^4$ and $R^5$ are hydrogen.

10. The compound of claim 8, wherein Y is —$C(O)NH_2$ and Z is —$NH_2$.

11. The compound of claim 10, wherein m is 0.

12. The compound of claim 10, wherein m is 1 and $R^6$ is halo, alkyl, alkoxy, haloalkyl, nitro, cyano, 2-cyanoethyl, or morpholinomethyl.

13. The compound of claim 8, wherein said compound is of the formula III.

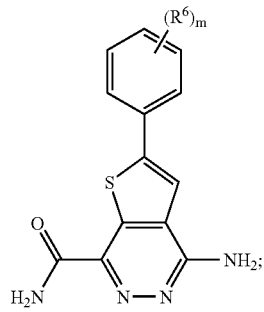

wherein m and $R^6$ are as recited in claim 8.

14. The compound of claim 13, wherein m is 0.

15. The compound of claim 13, wherein m is 1 and $R^6$ is fluoro, methoxy, nitro, cyano, 2-cyanoethyl, or morpholinomethyl.

16. A pharmaceutical composition comprising a pharmaceutically acceptable carrier or excipient and a compound of claim 1.

* * * * *